US010040689B2

United States Patent
Harder et al.

(10) Patent No.: US 10,040,689 B2
(45) Date of Patent: Aug. 7, 2018

(54) PROCESS FOR PREPARING MONOHYDROGENTRIHALOSILANES

(71) Applicant: Dow Corning Corporation, Midland, MI (US)

(72) Inventors: Patrick Harder, Saginaw, MI (US); Tyler Swenson, Midland, MI (US); David Williams, Midland, MI (US)

(73) Assignee: Dow Silicones Corporation, Midland, MI (US)

( * ) Notice: Subject to any disclaimer, the term of this patent is extended or adjusted under 35 U.S.C. 154(b) by 0 days.

(21) Appl. No.: 15/510,370

(22) PCT Filed: Nov. 25, 2015

(86) PCT No.: PCT/US2015/062569
§ 371 (c)(1),
(2) Date: Mar. 10, 2017

(87) PCT Pub. No.: WO2016/099833
PCT Pub. Date: Jun. 23, 2016

(65) Prior Publication Data
US 2017/0283268 A1    Oct. 5, 2017

Related U.S. Application Data

(60) Provisional application No. 62/094,431, filed on Dec. 19, 2014.

(51) Int. Cl.
*C01B 33/107*    (2006.01)
*C08G 77/04*    (2006.01)
(Continued)

(52) U.S. Cl.
CPC ......... *C01B 33/1071* (2013.01); *B01J 8/002* (2013.01); *B01J 23/72* (2013.01); *C08G 77/04* (2013.01)

(58) Field of Classification Search
CPC .......................... C01B 33/1071; C08G 77/04
See application file for complete search history.

(56) References Cited

U.S. PATENT DOCUMENTS 2,380,995 A    8/1945    Rochow
2,389,931 A    11/1945    Reed et al.
(Continued)

FOREIGN PATENT DOCUMENTS

GB    673436 A    6/1952
GB    945618 A    1/1964
(Continued)

OTHER PUBLICATIONS

Extended European Search report from corresponding European 15870627.5 application, dated May 17, 2018.

*Primary Examiner* — Ngoc-Yen Nguyen
(74) *Attorney, Agent, or Firm* — Catherine U. Brown

(57) ABSTRACT

A process for preparing a product including a monohydrogentrihalosilane is disclosed. The process includes the steps of: 1) initially charging a reactor with a contact mass including both fresh silicon and recycled contact mass, where the recycled contact mass is obtained from during or after a production phase of an inorganic Direct Process reaction for production of a monohydrogentrihalosilane; and thereafter 2) feeding to the reactor a hydrogen halide and additional fresh silicon, thereby forming the product.

12 Claims, 1 Drawing Sheet

(51) Int. Cl.
   *B01J 8/00*   (2006.01)
   *B01J 23/72*  (2006.01)

(56)        References Cited

U.S. PATENT DOCUMENTS

| | | | |
|---|---|---|---|
| 3,133,109 | A | 5/1964 | Dotson |
| 4,281,149 | A | 7/1981 | Shade |
| 4,307,242 | A | 12/1981 | Shah et al. |
| 4,390,510 | A | 6/1983 | Ritzer et al. |
| 4,602,101 | A | 7/1986 | Halm et al. |
| 4,762,940 | A | 8/1988 | Halm et al. |
| 4,946,978 | A | 8/1990 | Halm et al. |
| 5,160,720 | A | 11/1992 | Halm et al. |
| 5,243,061 | A * | 9/1993 | Webb ............... C07F 7/16 556/472 |
| 5,312,948 | A | 5/1994 | Freebume et al. |
| 5,712,405 | A | 1/1998 | Nakayama et al. |
| 5,777,146 | A | 7/1998 | Straussberger et al. |
| 5,783,721 | A | 7/1998 | Tsumura et al. |
| 5,871,705 | A | 2/1999 | Sakata et al. |
| 5,986,123 | A | 11/1999 | Nakayama et al. |
| 6,090,966 | A | 7/2000 | Nakanishi et al. |
| 6,252,102 | B1 | 6/2001 | Kalchauer et al. |
| 6,433,205 | B1 | 8/2002 | Brinson et al. |
| 6,447,846 | B2 * | 9/2002 | Nakamura ........... C09D 183/04 257/E21.262 |
| 6,465,674 | B1 | 10/2002 | Kalchauer et al. |
| 7,623,495 | B2 | 11/2009 | Toshimitsu et al. |
| 8,043,591 | B2 | 10/2011 | Pflugler et al. |
| 8,226,920 | B1 | 7/2012 | Kamei et al. |
| 2010/0290970 | A1 | 11/2010 | Staffin et al. |
| 2011/0158884 | A1 | 6/2011 | Bentley et al. |
| 2011/0180249 | A1 * | 7/2011 | Yoshida ............... C09D 5/028 165/185 |
| 2013/0121908 | A1 * | 5/2013 | Kamei ............. C01B 33/10763 423/342 |
| 2013/0156675 | A1 | 6/2013 | Breneman |

FOREIGN PATENT DOCUMENTS

| | | |
|---|---|---|
| GB | 1530986 A | 11/1978 |
| GB | 2153697 A | 8/1985 |

* cited by examiner

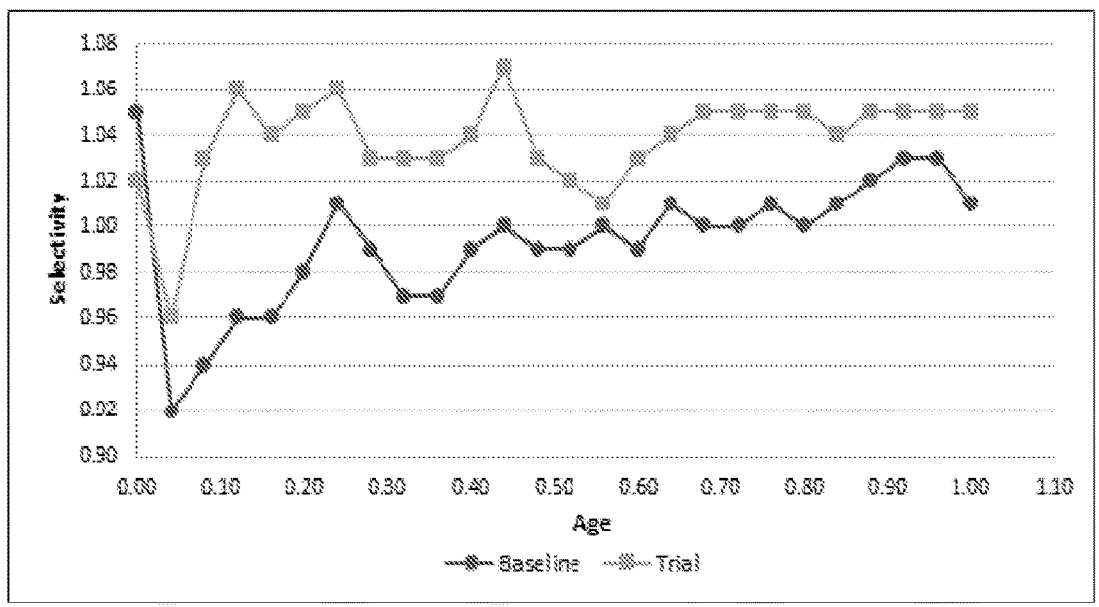

PROCESS FOR PREPARING MONOHYDROGENTRIHALOSILANES

This application is a U.S. national stage filing under 35 U.S.C. § 371 of PCT Application No. PCT/US15/062569 filed on 25 Nov. 2015, which claims the benefit of U.S. Provisional Patent Application No. 62/094,431 filed 19 Dec. 2014 under 35 U.S.C. § 119 (e). PCT Application No. PCT/US15/062569 and U.S. Provisional Patent Application No. 62/094,431 are hereby incorporated by reference.

TECHNICAL FIELD

A process for preparing monohydrogentrihalosilanes by the inorganic Direct Process reaction is described herein. The selectivity toward monohydrogentrihalosilanes in the product of the inorganic Direct Process reaction is increased by the process. Monohydrogentrihalosilanes, such as monohydrogentrichlorosilane ($HSiCl_3$), produced by this process are useful as reactants for use in the preparation of valuable silicon products, such as polycrystalline silicon and polysiloxane resin.

BACKGROUND

Methods of preparing halosilanes are known in the art. Typically, halosilanes are produced commercially by the Mueller-Rochow Direct Process, which comprises passing a halide compound over zero-valent silicon ($Si^0$) to obtain a gas-solid direct contact between the $Si^0$ and the halide compound, resulting in the production of a mixture of halosilane compounds. The typical process for making the $Si^0$ used in the Direct Process involves carbothermic reduction of silicon dioxide ($SiO_2$) in an electric arc furnace. In a typical submerged arc furnace process, a mixture of carbon and $SiO_2$ is added to the top of the furnace. Both alternating current (AC) arc furnaces and direct current (DC) power sources may be used. U.S. Pat. No. 5,009,703 and the references cited therein describe production of $Si^0$ from $SiO_2$. The overall reaction can be represented as follows: $SiO_2 + 2C \rightarrow Si^0 + 2CO$. The $Si^0$ produced by this process is typically at least 98% pure.

Products, which include mixtures of halogenated silicon containing compounds, are produced by the Direct Process. When an organohalide is used as the halide compound, a copper catalyst and various optional promoters are added to the $Si^0$, and the product includes a mixture of organohalosilanes (organic Direct Process). When a hydrogen halide is used as the halide compound, the product includes a mixture of inorganic hydrogen-functional halosilanes (inorganic Direct Process). Typically, catalyst and promoters are not added to the $Si^0$ in the inorganic Direct Process.

Frequently, the inorganic Direct Process has been run in a continuous or semi-batch mode. During a production campaign, the inorganic Direct Process is initiated by charging a reactor with a contact mass comprising fresh silicon that is free of catalyst and promoters, e.g., $Si^0$ prepared by carbothermic reduction as described above. A hydrogen halide and additional fresh silicon are added to the reactor to produce the product. When selectivity toward monohydrogentrihalosilane in the product drops to an undesirable level, the production campaign is ended by shutting down the reactor and discarding any silicon remaining therein.

SUMMARY OF THE INVENTION

A process for preparing a product comprising a monohydrogentrihalosilane of formula $HSiX_3$, where each X is independently a halogen atom with improved selectivity is described herein. The process comprises: 1) charging a reactor with a contact mass of fresh silicon (e.g., $Si^0$ as described above) and recycled contact mass, where the recycled contact mass is obtained from an inorganic Direct Process reaction for production of a monohydrogentrihalosilane; and, thereafter, 2) feeding to the reactor a hydrogen halide and additional fresh silicon, thereby forming the product. The fresh silicon may be the Si0 described above.

BRIEF DESCRIPTION OF THE DRAWINGS

FIG. 1 is a graph showing the normalized monomer selectivity (y-axis) vs. normalized age of the contact mass (x-axis) results of Comparative Example 1 (Normalized Average Baseline Selectivity) and Example 1 (Normalized Average Trial Selectivity). FIG. 1 is a graph of the data from Table 1 and Table 2, which compares the normalized monomer selectivity over the normalized age from 0 to 1 for the baseline and trial cases. The line labeled Baseline Average Selectivity represents the results of Comparative Example 1, and the line labeled Trial Average Selectivity represents the results of Example 1. This graph shows that the 'drop in monomer selectivity' is significantly reduced using the process described herein.

DETAILED DESCRIPTION OF THE INVENTION

It is desirable to run the inorganic Direct Process in a continuous or semi-batch mode in campaigns that continue for as long as possible to maximize the yield of product between reactor shutdowns. One of the problems associated with the inorganic Direct Process is controlling the selectivity. Selectivity refers to the amounts of the halogenated silicon containing compounds in the product. There is an industry need to produce monohydrogentrihalosilane, and reduce the number of other halogenated silicon containing compounds produced. The other halogenated silicon containing compounds include monomeric halosilane compounds such as dihydrogendihalosilanes and silicon tetrahalides, and polymeric halogenated silicon containing compounds such as polysilanes and polysiloxanes. For example, when HCl is used as the hydrogen halide, the product of the inorganic Direct Process may include, in addition to monohydrogentrichlorosilane ($HSiCl_3$); other monomeric halosilane compounds such as dihydrogendichlorosilane ($H_2SiCl_2$) and silicon tetrachloride ($SiCl_4$). The product may further include polymeric chlorinated silicon containing compounds, such as polychlorosilanes such as hexachlorodisilane ($Si_2Cl_6$) and/or polychlorosiloxanes such as hexachlorodisiloxane ($Si_2OCl_6$), and partially hydrogenated polychlorosilanes and polychlorosiloxanes, such as tetrachlorodisiloxane ($H_2Si_2OCl_4$) and pentachlorodisiloxane ($HSi_2OCl_5$).

In the inorganic Direct Process, reactivity (e.g., to consume the hydrogen halide and $Si^0$), and selectivity toward producing monohydrogentrichlorosilane in the product are typically relatively high at the beginning of the process. However, after a relatively short duration, monomer selectivity will drop to an undesirable level, such that the amounts of other halogenated silicon containing compounds (relative to the amount of monohydrogentrihalosilane) in the product increase. In particular, the amount of silicon tetrahalide relative to monohydrogentrihalosilane increases in the product, and this phenomenon, referred to herein as the 'drop in monomer selectivity', will occur for certain duration, after which monomer selectivity will increase to a desired level, thereby increasing the amount of monohydrogentrihalosilane in the product (i.e., the amounts of other halogenated silicon containing compounds decrease relative to the amount of monohydrogentrihalosilane in the product, particularly the amount of silicon tetrahalide decreases). The process will then continue for a longer duration with the desired monomer selectivity in the product. This is referred to herein as the 'production phase'. After the production phase, the amount of polymeric halogenated silicon containing compounds will increase in the product, thus the overall selectivity will drop to an undesirable level (referred to herein as the 'drop in overall selectivity'). Overall selectivity refers to the production of monomeric halosilane compounds as compared to polymeric halogenated silicon containing compounds in the product. When the drop in monomer selectivity occurs, the duration of the drop in monomer selectivity, the duration of the production phase, and when the drop in overall selectivity occurs will each depend on various factors including the type and size of reactor selected, any impurities in the fresh silicon used, the hydrogen halide feed rate selected, the amount of silicon in the reactor, and process temperature selected. However, the inventors found consistently that the drop in monomer selectivity occurs regardless of the factors (described above) and process conditions selected. Therefore, there is an industry need to reduce or eliminate the drop in monomer selectivity when performing the inorganic Direct Process in order to provide a consistent amount of monohydrogentrihalosilane in the product produced throughout a campaign.

Without wishing to be bound by theory, it was thought that the drop in overall selectivity was caused by build up of impurities in the contact mass in the reactor used for the inorganic Direct Process reaction. These impurities may have been introduced with the fresh silicon used as reactant. The $Si^0$ produced by the carbothermic reduction process described above may be used as fresh silicon in this process, and this $Si^0$ is typically at least 98% pure. However, the $Si^0$ contains one or more impurities in addition to the silicon, e.g., the $Si^0$ further comprises >0% to <2% of one or more of iron (Fe), aluminium (Al), calcium (Ca) and/or titanium (Ti). As a campaign progresses, silicon reacts and is removed from the reactor in the form of the product. However, some or all of the impurities do not react and build up in the contact mass in the reactor as more fresh silicon containing the impurities is added to the reactor. When this amount builds up to a high enough level, the drop in overall selectivity occurs. When the drop in overall selectivity occurs, the silicon is deemed spent (referred to herein "spent silicon") because even if the campaign is continued, overall selectivity will not increase after the drop in overall selectivity occurs. However, the inventors surprisingly found that by combining spent silicon with fresh silicon at the beginning of a subsequent campaign (instead of beginning the subsequent campaign with only fresh silicon), the drop in monomer selectivity was minimized or eliminated in the subsequent campaign without producing additional polymeric halogenated silicon containing compounds or otherwise detrimentally impacting the overall selectivity. This is particularly unexpected because the spent silicon was obtained during the portion of a campaign in which overall selectivity is undesirable (i.e., the spent silicon was obtained after the drop in overall selectivity occurred, therefore increased amounts of polymeric halogenated silicon containing compounds were being formed in the product). Since the spent silicon was obtained from a portion of the campaign in which overall selectivity was poor, it was surprising to find combining this spent silicon with fresh silicon improved monomer selectivity (by minimizing or eliminating the drop in monomer selectivity) without detrimentally impacting overall selectivity in a subsequent campaign. This is also particularly surprising because the inorganic Direct Process is typically uncatalyzed, unlike the organic Direct Process described above. In contrast to the organic Direct Process, the process described herein does not require the addition of a copper catalyst or a promoter to the fresh silicon to achieve high yields or improve selectivity. Therefore, the spent silicon of the inorganic Direct Process does not contain catalyst and/or promoter that can be recycled in a subsequent campaign.

Furthermore, the inventors surprisingly found that adding spent silicon later in the process (e.g., during or after the drop in monomer selectivity, and/or during the production phase) could be detrimental to overall selectivity. Adding spent silicon to the reactor at any time in a campaign other than at the initial charge of contact mass resulted in more polymeric halogenated silicon containing compounds being formed in the product than would have occurred if the spent silicon had not been added later in the process.

The inventors further found that taking contact mass from the reactor during or after the production phase of a campaign (i.e., after the drop in monomer selectivity ended) would also improve monomer selectivity when combined with fresh silicon in the initial charge in the reactor at the beginning of a subsequent campaign. Without wishing to be bound by theory, it is thought that the impurities introduced into the reactor with the fresh silicon build up in the contact mass as a campaign progresses, and that after the first drop in monomer selectivity ends and the production phase of a campaign begins, the contact mass in the reactor contains sufficient impurities to improve monomer selectivity without detrimentally affecting overall selectivity, when used as a portion of an initial charge of contact mass for a subsequent campaign. Therefore, the process described herein may be performed using recycled contact mass, which is contact mass taken from inside the reactor during or after the production phase of a campaign when sufficient impurities have concentrated in the contact mass to provide the benefit of reducing or eliminating the drop in monomer selectivity.

The recycled contact mass may or may not be spent silicon. Recycled contact mass may be contact mass that is removed from the reactor during or after the production phase of a campaign. Alternatively, recycled contact mass may be left in the reactor if the reactor is shut down after the drop in monomer selectivity ends, but before the drop in overall selectivity occurs. The recycled contact mass may be up to 85% silicon with the balance being impurities that have concentrated during the campaign as silicon was reacted and removed from the reactor as product. Alternatively, recycled contact mass may be >0% to 85% silicon; alternatively 30% to 82% silicon, alternatively 30% to 80% silicon, alternatively 30% to 70% silicon; with the balance being impurities. Alternatively, recycled contact mass may be 40% to 85%. Alternatively, spent silicon may be used in the process described herein.

When the fresh silicon and recycled contact mass are combined to form an initial charge of contact mass in the reactor, the amounts of fresh silicon and recycled contact mass are selected to provide the initial charge of contact mass with a silicon content of 50% to 95%, alternatively 70% to 90%, alternatively 80% to 90%, alternatively 85% to 90%, alternatively 82% to 90%, and alternatively 80% to 85%; with the balances being impurities.

Therefore, the process described herein is a process for preparing a product comprising a monohydrogentrihalosilane of formula $HSiX_3$, where each X is independently a halogen atom. The process has improved monomer selectivity over the inorganic Direct Process practiced previously in which no recycled contact mass is charged in the reactor at the beginning of a campaign. In a first embodiment, the process comprises:

1) charging a reactor with a contact mass of fresh silicon and recycled contact mass, where the recycled contact mass is obtained during or after a production phase of an inorganic Direct Process reaction for production of a monohydrogentrihalosilane; and, thereafter, 2) feeding to the reactor a hydrogen halide and additional fresh silicon, thereby forming the product. More specifically, in a second embodiment, the process may comprise:

1) charging a reactor with a contact mass of fresh silicon and spent silicon, where the spent silicon is obtained after a drop in overall selectivity occurs in an inorganic Direct Process reaction for production of a monohydrogentrihalosilane; and, thereafter, 2) feeding to the reactor a hydrogen halide and additional fresh silicon, thereby forming the product.

The fresh silicon may be $Si^0$ obtained from the carbothermic reduction process described above. Particle size of the fresh silicon may be any particle size suitable for use in the reactor selected for the process. However, for example, when a fluidized bed reactor is used, the fresh silicon may have a particle size up to 150 micrometers (μm). Standard methods for producing fresh silicon in particulate form can be used, for example, the use of a roller or ball mill to grind silicon lumps. The fresh silicon may be further classified as to particle size distribution by means of, for example, screening or use of mechanical aerodynamic classifiers such as a rotating classifier.

Recycled contact mass is obtained from an inorganic Direct Process reaction for production of a monohydrogentrihalosilane. The recycled contact mass is obtained during or after the production phase of a campaign (e.g., not during or before the drop in monomer selectivity that occurs when a fresh silicon contact mass is used in the inorganic Direct Process). In one embodiment, all or a portion of the recycled contact mass is left in the reactor after a campaign ends (i.e., after the production phase, and after the hydrogen halide and fresh silicon are no longer fed to the reactor). The campaign may be ended during the production phase before the drop in overall selectivity occurs. Alternatively, the campaign may be ended after the drop in overall selectivity occurs (in which case the recycled contact mass left in the reactor will be spent silicon). Fresh silicon may then be added to the same reactor with the recycled contact mass, thereby forming the initial charge of contact mass including fresh silicon and recycled contact mass at the beginning of a subsequent campaign. In an alternative embodiment, the recycled contact mass is removed from the reactor, and all or a portion of the recycled contact mass is charged into a different reactor with fresh silicon to form a contact mass at the beginning of a different campaign. In the process described herein, recycled contact mass is only added in the initial charge in the reactor at the beginning of a campaign. Recycled contact mass is not added to a campaign after beginning to feed the hydrogen halide.

The process described herein may optionally further comprise a preheating step before step 2). In the process described herein, the contact mass in step 1) may optionally be heated for a certain time in an inert atmosphere at a temperature of 200° C. to 350° C., alternatively 200° C. to 280° C., before beginning to add the hydrogen halide to the reactor. Without wishing to be bound by theory, it is thought that preheating may improve reactivity and/or fluidization of the contents of the reactor.

Hydrogen halides are known in the art and are commercially available. The hydrogen halide may optionally be preheated and/or vaporized before it is fed into the reactor. The hydrogen halide may be hydrogen bromide (HBr), hydrogen chloride (HCl), or hydrogen iodide (HI). Alternatively, the hydrogen halide may be HCl.

The reaction of a hydrogen halide with a particulate contact mass is a surface reaction. More available silicon surface gives more potential for reaction in a given volume, so reaction rate is related to the specific surface area of the particles of silicon available. Smaller particles have high specific surface areas and react away quickly while larger particles have a lower specific surface area and a corresponding lower reaction rate. Furthermore, when the process is run a continuous or semi-batch mode, the particles of silicon spend a finite residence time in the reactor, therefore, faster reacting small particles are more likely to be consumed to give high silicon conversion (high yield) and consequently fewer unreacted particles of spent silicon.

In the process described herein, the product typically comprises more than one monomeric halosilane compound described by general formula $H_xSiX_{(4-x)}$, where subscript x has an average value of 0 to 3, and X is a halogen atom. Alternatively, each X may be a chlorine atom. When X is Cl, the monomeric halosilane compounds in the product include $H_2SiCl_2$, $HSiCl_3$, and $SiCl_4$. The product may further comprise polymeric halogenated silicon containing compounds, as described above, however, the product may predominantly comprise $HSiCl_3$ and $SiCl_4$.

The process may optionally further comprise one or more additional steps (in addition to the steps described above). The process may optionally further comprise: 3) feeding to the reactor additional hydrogen halide without fresh silicon after step 2). When this step is present, the amount of silicon in the contact mass is depleted. The process may optionally further comprise repeating steps 1) and 2) (and when present step 3)) one or more times in additional subsequent production campaigns.

The relative amounts of recycled contact mass and fresh silicon in the contact mass initially charged in the reactor at the beginning of a campaign may vary depending on factors including length of the campaign, rate at which the fresh silicon and hydrogen halide are fed to the reactor in step 2), whether step 3) is performed, reactor size, and whether the optional step of feeding additional hydrogen halide without fresh silicon is performed in the immediately preceding campaign (i.e., the campaign from which the spent silicon was obtained). However, the spent silicon may be present in an amount of 5% to 90% and the fresh silicon may be present in an amount of 5% to 95%. Alternatively, the spent silicon may be present in an amount of 10% to 60%, and the fresh silicon may be present in an amount of 40% to 90%, in the contact mass charged in the reactor at the beginning of a campaign. Alternatively, the recycled contact mass may be present in an amount of 5% to 95% and the fresh silicon may be present in an amount of 5% to 95% charged in the reactor at the beginning of a campaign. Alternatively, the recycled contact mass may be present in an amount of 10% to 90% and the fresh silicon may be present in an amount of 10% to 90% of the contact mass charged in the reactor. Alternatively, the recycled contact mass may be present in an amount of 15% to 85% and the fresh silicon may be present in an amount of 15% to 85% of the contact mass charged in the reactor. Alternatively, the recycled contact mass may be present in an amount of 20% to 80% and the fresh silicon may be present in an amount of 20% to 80% of the contact mass charged in the reactor.

The process may be performed under conventional pressure and temperature conditions for the inorganic Direct Process, for example temperature in step 2) and/or optional step 3) of feeding additional hydrogen halide without fresh silicon) may be 250° C. to 350° C., alternatively 280° C. to 340° C. Pressure is not critical, however, the pressure may range from 0 to 10 atmospheres gauge, alternatively 1 to 5 atmospheres gauge.

The process may further comprise enabling the product to leave the reactor whereby the monohydrogentrihalosilane, hydrogen, and unreacted hydrogen halide elutriate a proportion of the contact mass. For example, when the process is run in a continuous or semi-batch mode, the process further comprises removing product from the reactor during step 2). Fresh silicon is added to the reactor during step 2) to replace silicon consumed by the inorganic Direct Process reaction and silicon elutriated with the product. Fresh silicon may be added continuously or intermittently during step 2). However, in this process contact mass need not be removed from the reactor other than by elutriation during step 2).

Alternatively, the process may further comprise recovering the monohydrogentrihalosilane from the product. Recovering the monohydrogentrihalosilane may be performed after step 2), and/or after step 3), when step 3) is present. Recovering may be performed by conventional means, such as distillation of the product. The monohydrogentrihalosilane is useful as a reactant for the production of valuable silicon materials such as polycrystalline silicon and/or polysiloxane resin. The process may optionally further comprise recovering other halogenated silicon containing compounds (in addition to the monohydrogentrihalosilane) from the product. For example, silicon tetrahalides, such as silicon tetrachloride, may be isolated and used as reactants for fumed silica production. Alternatively, the product (e.g., including a mixture of $HSiCl_3$ and $SiCl_4$) may be used as a reactant for fumed silica production without isolation of the monomeric halosilane species in the product.

The process may optionally further comprise removing a portion of the contact mass from the reactor during the production phase of a campaign. The contact mass removed may be replaced with fresh silicon (e.g., by increasing the feed rate of the fresh silicon fed to the process in step 2)). The process may optionally further comprise a purging step and/or a treating step. "Purging" means to introduce a gas stream into a container to remove unwanted materials. Unwanted materials that may be present in the reactor are, for example, $O_2$ and $H_2O$. Purging the reactor may be done before step 1), after step 1) and before step 2) and/or after step 2); alternatively, before step 1). Purging may be accomplished with an inert gas, such as argon, nitrogen, or helium or with a reactive gas, such as an inorganic halosilane, e.g., silicon tetrachloride, which reacts with moisture thereby removing it. "Treating" means to introduce a gas stream into a container to pre-treat a component before contacting the component with another component. Treating before step 1) may be done to at least partially remove any oxide layer that may be present on the surfaces of the particles of fresh silicon. In the first embodiment, treating may be performed after step 1) and before step 2). In the second embodiment, treating may be performed after step 1) and before step 2).

The process described herein may be performed in any reactor suitable for contacting gases and solids. For example, the reactor can be a packed bed reactor, a stirred bed reactor, a vibrating bed reactor, a moving bed reactor, a re-circulating bed reactor, or a fluidized bed reactor. Alternatively, the reactor may be a fluidized bed reactor. The contact mass and the hydrogen halide may be contacted by, e.g., fluidizing the contact mass in a fluidized bed reactor. The hydrogen halide, or a mixture of hydrogen halide and an inert gas may be used to fluidize the contact mass. For example, suitable inert gases include nitrogen, helium, argon, and mixtures thereof. Different campaigns may be performed in the same reactor. Alternatively an initial campaign and a subsequent campaign may be performed in different reactors.

EXAMPLES

These examples are intended to illustrate some embodiments of the invention and should not be interpreted as limiting the scope of the invention set forth in the claims.

Comparative Example 1—Production of $HSiCl_3$ Using the Direct Process with no Recycled Contact Mass A fluidized bed reactor was charged with a contact mass of fresh silicon powder. The fresh silicon was fluidized with an inert gas and heated to 240° C. The reaction was initiated with the addition of hydrogen chloride gas and maintained in a temperature range of 280° C. to 320° C. during the campaign. The inventory of contact mass in the reactor was maintained by continually adding more fresh silicon to replace silicon that was reacted in the chlorosilane synthesis reaction and that left the reactor with the product due to elutriation. This process was repeated three more times using the same conditions, for a total of four campaigns as controls. The results of these four campaigns were averaged, and the average results are presented in Table 1 below. The normalized age from 0 to 1 covers the 'drop in monomer selectivity' and the subsequent 'increase in monomer selectivity' to the desired level for each campaign. The monomer selectivity was also normalized with 1 being the average monomer selectivity over the normalized age from 0 to 1 for the four control campaigns.

TABLE 1

| Normalized Age | Normalized Average Baseline Monomer Selectivity |
|---|---|
| 0.00 | 1.05 |
| 0.04 | 0.92 |
| 0.08 | 0.94 |
| 0.12 | 0.96 |
| 0.16 | 0.96 |
| 0.20 | 0.98 |
| 0.24 | 1.01 |
| 0.28 | 0.99 |
| 0.32 | 0.97 |
| 0.36 | 0.97 |
| 0.40 | 0.99 |
| 0.44 | 1.00 |
| 0.48 | 0.99 |
| 0.52 | 0.99 |
| 0.56 | 1.00 |
| 0.60 | 0.99 |
| 0.64 | 1.01 |
| 0.68 | 1.00 |
| 0.72 | 1.00 |
| 0.76 | 1.01 |
| 0.80 | 1.00 |
| 0.84 | 1.01 |
| 0.88 | 1.02 |

TABLE 1-continued

| Normalized Age | Normalized Average Baseline Monomer Selectivity |
|---|---|
| 0.92 | 1.03 |
| 0.96 | 1.03 |
| 1.00 | 1.01 |

Example 1

After the production phase of a campaign performed as described above in Comparative Example 1, the reactor was shut down, and recycled contact mass remained in the reactor. A portion of this recycled contact mass was removed from the reactor. However, 35% of the recycled contact mass remaining after the campaign as described in Comparative Example 1 was left in the reactor. The reactor was then charged with an additional amount of the same fresh silicon powder as described above in Comparative Example 1. As a result, the reactor contained an amount of fresh silicon:recycled contact mass of 2:1. A campaign was then performed in the reactor using the same conditions as the campaign described above in Comparative Example 1. This campaign was able to reach target selectivity and able to start the production phase in less than 10% of the time required for the control campaigns described in Comparative Example 1. The trial was repeated again, but this time 13% of the recycled contact mass from the previous campaign was left in the reactor. The reactor was then charged with an amount of fresh silicon sufficient to provide a ratio of fresh silicon:recycled contact mass of 8:1. This campaign showed similar results, also reaching selectivity sufficient to start the production phase at a Normalized Age less than 100% of the Normalized Age of the control sample in Comparative Example 1. The averaged results of these two trials are shown below in Table 2.

TABLE 2

| Normalized Age | Normalized Average Trial Monomer Selectivity |
|---|---|
| 0.00 | 1.02 |
| 0.04 | 0.96 |
| 0.08 | 1.03 |
| 0.12 | 1.06 |
| 0.16 | 1.04 |
| 0.20 | 1.05 |
| 0.24 | 1.06 |
| 0.28 | 1.03 |
| 0.32 | 1.03 |
| 0.36 | 1.03 |
| 0.40 | 1.04 |
| 0.44 | 1.07 |
| 0.48 | 1.03 |
| 0.52 | 1.02 |
| 0.56 | 1.01 |
| 0.60 | 1.03 |
| 0.64 | 1.04 |
| 0.68 | 1.05 |
| 0.72 | 1.05 |
| 0.76 | 1.05 |
| 0.80 | 1.05 |
| 0.84 | 1.04 |
| 0.88 | 1.05 |
| 0.92 | 1.05 |
| 0.96 | 1.05 |
| 1.00 | 1.05 |

INDUSTRIAL APPLICABILITY

It can be readily seen in Comparative Example 1 that the average campaign is unable to achieve selectivity above baseline until 64% through this period. However, in Example 1, the process described herein shows an average selectivity greater than 1 during this period, representing an improvement to the process of Comparative Example 1.

The Brief Summary of the Invention and the Abstract are hereby incorporated by reference. All ratios, percentages, and other amounts are by weight, unless otherwise indicated. The articles 'a', 'an', and 'the' each refer to one or more, unless otherwise indicated by the context of the specification.

The disclosure of ranges includes the range itself and also anything subsumed therein, as well as endpoints. For example, disclosure of a range of 2.0 to 4.0 includes not only the range of 2.0 to 4.0, but also 2.1, 2.3, 3.4, 3.5, and 4.0 individually, as well as any other number subsumed in the range. Furthermore, disclosure of a range of, for example, 2.0 to 4.0 includes the subsets of, for example, 2.1 to 3.5, 2.3 to 3.4, 2.6 to 3.7, and 3.8 to 4.0, as well as any other subset subsumed in the range.

With respect to any Markush groups relied upon herein for describing particular features or aspects of various embodiments, it is to be appreciated that different, special, and/or unexpected results may be obtained from each member of the respective Markush group independent from all other Markush members. Each member of a Markush group may be relied upon individually and or in combination with any other member or members of the group, and each member provides adequate support for specific embodiments within the scope of the appended claims. For example, disclosure of the Markush group: alkyl, aryl, and carbocyclic includes the member alkyl individually; the subgroup alkyl and aryl; and any other individual member and subgroup subsumed therein.

It is also to be understood that any ranges and subranges relied upon in describing various embodiments of the present disclosure independently and collectively fall within the scope of the appended claims, and are understood to describe and contemplate all ranges including whole and/or fractional values therein, even if such values are not expressly written herein. The enumerated ranges and subranges sufficiently describe and enable various embodiments of the present disclosure, and such ranges and subranges may be further delineated into relevant halves, thirds, quarters, fifths, and so on. As just one example, a range "of 250 to 350" may be further delineated into a lower third, i.e., from 250 to 283, a middle third, i.e., from 284 to 317, and an upper third, i.e., from 318 to 350, which individually and collectively are within the scope of the appended claims, and may be relied upon individually and/or collectively and provide adequate support for specific embodiments within the scope of the appended claims. In addition, with respect to the language which defines or modifies a range, such as "at least," "greater than," "less than," "no more than," and the like, it is to be understood that such language includes subranges and/or an upper or lower limit. As another example, a range of "up to 85%" inherently includes a subrange from 0.1% to 85%, a subrange from 30% to 50%, a subrange from 33% to 57%, and so on, and each subrange may be relied upon individually and/or collectively and provides adequate support for specific embodiments within the scope of the appended claims. Finally, an individual number within a disclosed range may be relied upon and provides adequate support for specific embodiments within the scope of the appended claims. For example, a range of "1 to 9" includes various individual integers, such as 3, as well as individual numbers including a decimal point (or fraction), such as 4.1, which may be relied upon and provide adequate support for specific embodiments within the scope of the appended claims.

The subject matter of all combinations of independent and dependent claims, both singly and multiply dependent, is expressly contemplated but is not described in detail for the sake of brevity. The disclosure has been described in an illustrative manner, and it is to be understood that the terminology which has been used is intended to be in the nature of words of description rather than of limitation. Many modifications and variations of the present disclosure are possible in light of the above teachings, and the disclosure may be practiced otherwise than as specifically described.

The invention claimed is:

1. A process for preparing a product comprising a monohydrogentrihalosilane of formula $HSiX_3$, where each X is independently a halogen atom, where the process comprises:
   1) charging a reactor with an initial charge of contact mass of fresh silicon and adding recycled contact mass only to the initial charge, where the recycled contact mass is obtained during or after a production phase of an inorganic Direct Process reaction; and thereafter
   2) feeding to the reactor a hydrogen halide of formula HX and additional fresh silicon, thereby forming the product.

2. The process of claim 1, where the contact mass in step 1) contains 50 weight % to 95 weight % silicon.

3. The process of claim 1, where the recycled contact mass is spent silicon.

4. The process of claim 1, further comprising: step 3) feeding to the reactor additional hydrogen halide without fresh silicon after step 2).

5. The process of claim 1, where the reactor is a fluidized bed reactor.

6. The process of claim 1, further comprising recovering the monohydrogentrihalosilane from the product.

7. The process of claim 1, where each X is chlorine.

8. A process for preparing a product comprising a monohydrogentrihalosilane of formula $HSiX_3$, where each X is independently a halogen atom, the process comprises:
   1) charging a reactor with an initial charge of contact mass of fresh silicon and spent silicon, where the spent silicon is obtained no earlier than beginning a drop in overall selectivity of an inorganic Direct Process reaction campaign; and thereafter
   2) feeding to the reactor a hydrogen halide of formula HX and additional fresh silicon, thereby forming the product.

9. The process of claim 8, where the contact mass in step 1) contains 50 weight % to 95 weight % silicon.

10. The process of claim 8, further comprising: step 3) feeding to the reactor additional hydrogen halide without fresh silicon after step 2).

11. The process of claim 8, where the reactor is a fluidized bed reactor.

12. The process of claim 8, further comprising recovering the monohydrogentrihalosilane from the product.

* * * * *